Oct. 15, 1974 M. KRILOFF Plant Pat. 3,640
ROSE PLANT
Filed Oct. 17, 1973
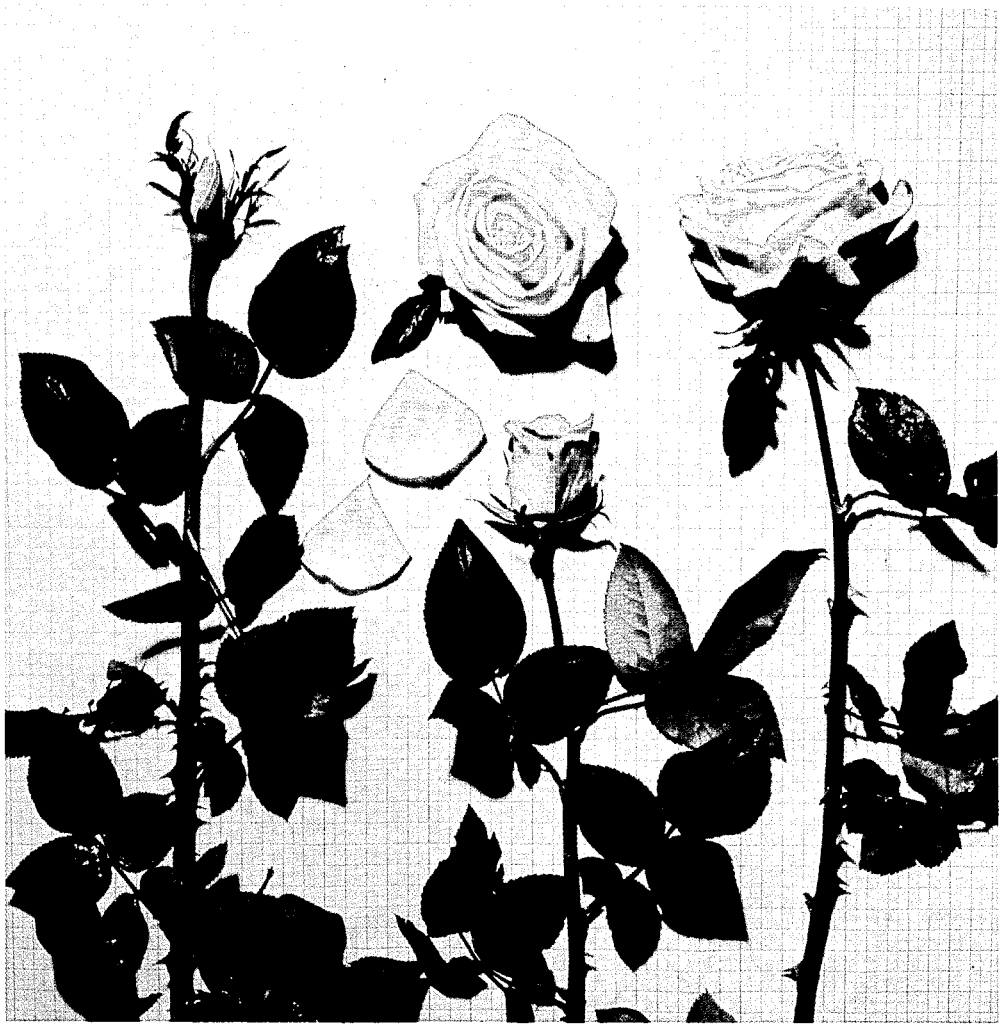

United States Patent Office

Plant Pat. 3,640
Patented Oct. 15, 1974

3,640
ROSE PLANT

Michel Kriloff, Chemin des Brusquets-St. Maymes, Les Roses, 06600 Antibes, France Filed Oct. 17, 1973, Ser. No. 407,261
Int. Cl. A01h 5/00
U.S. Cl. Plt.—11 1 Claim The present invention relates to a new and distinct variety of rose plant.

The present invention provides a new variety of rose plant for the production of cut flowers and ornamental growing plants, which is an improvement on varieties of rose plants already cultivated. In particular, in accordance with the requirements of world-wide markets for cut flowers, the present invention provides a new variety of rose plant which has improved vegetative and reproductive qualities compared to varieties already cultivated, with a special color tone of the flowers, which is very much sought after and which permits the realization of maximum profit from the sale of the plants and their cut flowers.

After numerous attempts, it has been possible according to the present invention to produce a hybrid variety of rose plant, by crossing the variety known commercially as "KRIra" as the female plant, with an unclassified variety as the pollenating plant, thereby to produce the first plant according to the present invention, in which was embodied the desired characteristics.

The plant of the present invention may be easily reproduced and multiplied in any desired number having all the characteristics of the original plant, by means of vegetative multiplication methods of plants employed in floriculture and especially by grafting of shoots onto host rose plants which are hardy in the soil where it is desired to cultivate the present invention.

Thus reproduced, the present invention transmits with constancy and fidelity all the distinctive characteristics to successive generations, thereby permitting the production of large homogeneous plant populations which are stable as to their characteristics. Thus the rose plant of the present invention is well adapted for industrial floriculture, for the production of cut flowers, or for plants destined for use in landscaping and gardening.

The characteristics which in their unique combination distinguish the rose plant variety according to the present invention and thus permit its ready identification, are set forth in the specification that follows, which in turn describes a group of plants industrially cultivated and grafted for about two years on Rosa Indica major growing in dirt in greenhouses at Saint-Maymes (Alpes-Maritimes, France) and observed and described in the month of January.

Thus it is to this seasonable condition and these conditions of floriculture that reference must be made for purposes of comparison with the rose plant described hereinafter. It is of course to be understood that there will be normal fluctuations in the plant characteristics according to climate, soil and methods of culture, but these do not modify in any essential respect the present invention, as the repetition of the culture of the plant under the conditions described hereafter will permit ready identification of the plant according to the following characteristics.

The color nomenclature in the following description is in accordance with the tables in the reference "Horticultural Colour Chart" by Robert F. Wilson (hereinafter referred to as HCC) except when the color is not described in that work, or when the nature of the color is sufficiently clearly indicated by ordinary usage.

Reference is also had to the accompanying drawing, forming a part hereof, which shows various portions of the plant and the condition of the plant budded and in bloom.

The characteristics are as follows:

*Classification*—Hybrid tea rose.
*Derivation*—"KRIra" crossed with an unclassified hybrid.

PLANT

*Overall Aspect*—Bushy, very vigorous, rapidly growing, very thin, erect and vertical. Vegetation heavily bushy in the higher part of the plant.

*Average Height*—180 to 250 cm. for full grown plants, cultivated under the indicated conditions.

*Roots*—Of medium number and medium branches, extending deep into the soil, about 50 to 60 cm. long and of a diameter at the top of about 2 to 10 mm. The bearded portions are long, of medium thickness and medium in number.

*Principal Stem*—Of variable form and dimensions according to the species which receives the graft. In the described plants, the principal stem was constituted by the cutting of Rosa Indica major, 20 to 25 cm. long and with a diameter at the base of 12 to 15 mm.

*Principal Branches*—Numerous, 8 to 10 in number, branching outward from the point of graft or from the base of other primary branches, somewhat divergent from the axis of the plant at their base, and then more vertical and parallel. Of medium thickness with little variation from the base to the top. The primary branches are articulated in sections 50 to 70 mm. long whose joints are moderately differentiated, projecting somewhat from the branches.

The average dimensions of the principal branches are, as to length, from the base to the summit 50 to 80 cm. and as to average diameter, 8 to 15 mm. at the base. The skin or peel of the principal branches is of medium thickness, smooth, glaborous, satiny, and pruinose in places.

The thorns are numerous and of uniform dimension, scattered along the branches but a bit more concentrated toward the base of the branches. The thorns are triangular, sharply pointed, differentiated, and almost at a right angle to the branches. The lower side of the thorns is concave while the upper side is straight or slightly concave. The thorns are difficult to detach from the stems and have average dimensions such that their average length is 8 to 10 mm. and their average width 9 to 12 mm. Their thickness is 3 to 5 mm. The base of the thorns is elliptical with the largest part up. The small thorns have a length of 1 to 5 mm., a width of 1 to 3 mm., and a thickness of ½ to 1 mm., and are of the same shape as the large thorns. In color, the thorns are hazel with touches of dark chestnut. In texture, the thorns are robust, almost woody, and rigid.

*Floral Branches*—Average 3 to 5 in number on each primary branch, more numerous on the upper part of the primary branches and closely spaced. In form, the floral branches are subcylindrical, robust, straight or slightly sinuous and sometimes slightly angled in correspondance to the nodes or joints, of medium thickness, and jointed into sections or internodes whose average length is 40 to 60 mm. The average dimensions of the floral branches are 100 to 150 cm. long to the base of the flower, and the average diameter, at the base, is 8 to 10 mm. The skin or peel of the floral branches is smooth, glabrous, opaque or slightly satiny, and pruinose in places. The color of the floral branches is close to Parsley Green (HCC, page 193, shades 00962/1–2–3) with overtones, in places, of Spinach Green (HCC, page 187, shades 0960–0960/1–2–3) and touched, in places, with Garnet Brown (HCC, page 192, shades 00918/2–3).

The thorns on the floral branches are numerous, generally large, intermixed with smaller thorns, scattered irregularly on the branches and more frequently on the lower parts of the branches. They average 5 to 10 per internode and are difficult to dislodge from the stem. The thorns are triangular, slightly concave on the lower side, sharply pointed, differentiated, slightly inclined downwardly or at a right angle to the stem. The base of the thorns is lanceloate and is larger in its upper part. The larger thorns have an average length of 12 to 14 mm., an average width of 12 to 15 mm., and an average thickness of 4 to 6 mm. For the smaller thorns, the average length is 4 to 6 mm., the average width 3 to 6 mm. and the average thickness 1 to 2 mm. The color of the thorns is more or less light hazel brown, tinged with chestnut. The texture of the thorns is spongy, rigid, and moderately resistant.

*Leaves*—Smaller and less numerous on the primary branches, and larger and more numerous on the floral branches on which they are abundantly arrayed along all the lengths. They are scattered on the branches individually corresponding to the nodes or joints. The leaves are large and moderately elongated, comprised by 3–5–7 leaflets inserted in opposed pairs, plus a terminal leaflet, on a robust and thick stem, at regular intervals. The average dimensions of the leaves are, on the primary branches, 100 to 130 mm. in length and 70 to 90 mm. wide. The leaves on the floral branches have an average length of 130 to 180 mm. and an average width of 100 to 140 mm. The configuration of the leaves is somewhat bent, at various angles to the stems from almost a right angle or somewhat downturned. The leaflets are flat in the foliate plane or slightly upturned relative thereto.

*Leaflets*—Limbus oval, elongated and wide, moderately sharp pointed at the end, little differentiated. Petiole short and sometimes sessile. The edges of the leaflets are dentate, the teeth being moderately numerous, simple, short and deeper adjacent the point of the leaflet. The average dimensions of the leaflets vary according to the state of development and according to the position on the stem, increasing from bottom to top and from the base of the stem toward the terminal leaflet.

The lower leaves, having 7 leaflets, have a first pair at the base of a length 18 to 20 mm. and a width 8 to 12 mm.; the second pair has a length 20 to 25 mm. and a width 10 to 15 mm.; the third pair a length 25 to 30 mm. and a width 18 to 20 mm.; while the terminal leaflet has a length 30 to 35 mm. and a width 20 to 25 mm.

The leaves of five leaflets comprise a first pair having a length 28 to 30 mm. and a width 20 to 25 mm.; a second pair having a length 25 to 40 mm. and a width 28 to 30 mm.; and a terminal leaflet having a length 45 to 50 mm. and a width 35 to 40 mm.

As to the medial and upper leaves, those having 7 leaflets have a first pair at the base whose leaflets are of a length 30 to 35 mm. and a width 40 to 45 mm.; a second pair having a length 40 to 45 mm. and a width 25 to 30 mm.; a third pair having a length 50 to 60 mm. and a width 35 to 45 mm.; and a terminal leaflet having a length 55 to 65 mm. and a width 40 to 50 mm. The leaves having 5 leaflets may have a first pair at the base of a length 45 to 55 mm. and a width 35 to 40 mm.; a second pair having a length 55 to 65 mm. and a width 40 to 50 mm.; and a terminal leaflet having a length 65 to 75 mm. and a width 40 to 60 mm.

The surface of the leaves, is, on the upper face, smooth, glaborous, and moderately glossy. The under face is smooth, glaborous, opaque, with pennate and reticulated ribs that project moderately on the limbus.

In color, the upper face is nearly Ivy Green (HCC, page 200, shades 0001060/1–2–3); and on the under surface, between Sage Green (HCC, page 198, shades 000861–000861/1–2) and Lavender Green (HCC, page 196, shades 000761–000761/1–2 .

In texture, the leaves are thick, coriaceous and resistant.

The steams are robust, sinuous, of semicircular cross section with a marked furrow in the upper face, pilose at the edges, and with moderately hooked tuft barbs on the under face.

The stipules are straight and adnate along the stem for about ⅓ of the length of the first internode. The earlets are straight, pilose at the edges, and moderately divergent from the stem.

FLOWER

*Overall Aspect*—A single flower, erect, straight relative to and at the end of the stem, sometimes accompanied by several secondary floral buds which are smaller and shorter than the principal stem, carried by lateral stems inserted at the highest joints of the stems, which often will not have floral buds.

*Closed Floral Bud*—Conical, hemispheric at the base, surmounted by floriaceous appendices which are irregular and laciniated. Other lateral appendices are lanceolate and diverage from the contour of the bud. The opening of the sepals is moderately advanced relative to that of the petals. The average dimensions of the closed buds are 30 to 35 mm. in length and 20 to 25 mm. in diameter.

*Partially Opened Bud*—In the form of an urn widened at the top. The external petals open outwardly and are of little if at all curled at their edges. The central petals are spiral and the center of the flower is closed, flat or a little raised. The average dimensions are 45 to 55 mm. in length and 35 to 45 mm. in diameter. The color is at the base Vermilion (HCC, page 18, shades 18–18/1) with shades of Scarlet Red (HCC, page 19, shades 19–19/1–2).

*Calyx*—Cup of medium dimensions, in the form of a hemisphere. Sepals are five in number, large, inserted on the edge of the cup, triangular, slightly lanceolate and very thinly pointed, continuing on in foliaceous appendices with dentate and laciniated edges, of a length up to 25 to 35 mm. and a width 10 to 12 mm. Other lanceolated and marginally dentated appendices diverge from the edges of the sepals. The edges of the sepals are tomentose. The average dimensions of the receptacle are 7 to 10 min. in length and 10 to 12 mm. in diameter; and of the sepals, 35 to 45 mm. in length without the appendices and 8 to 10 mm. wide at the base. The color of the upper surface is between Leek Green (HCC, page 197, shades 000858–000858/1) and Lavender Green (HCC, page 196, shades 000761–000761/1–2–3. The color of the under face is nearly Spinach Green (HCC, page 187, shades 0960–0960/1–2–3), sometimes with shades of Lettuce Green (HCC, page 176, shades 861–861/1–2). The surface of the upper face is covered with a fine white down. The lower face is smooth, opaque, and sometimes slightly gandulous. In texture, the calyx is of moderate thickness and resistant.

*Floral Peduncle*—Of medium length, straight, rigid, cylindrical, with small barbs of a length of 0.5 to 1 mm., which are tender. The medium length is 70 to 100 mm. and the diameter 4 to 5 mm.

*Open Corolla*—Very petalate, globose, with a raised center, and petals disposed in 8 to 10 superposed verticils. The shape is round, regular, and slightly star-shaped due to rounded or obtuse points formed by rolling of the petal edges. The petals swirl and curl moderately outwardly at the edges. The center of the flower is full and masks the stamens and the pistil. The profile of the flower is globose with the base petals slightly turned and rolled downwardly.

The average dimensions are, when completely open, 100 to 110 mm. in diameter and 55 to 65 mm. in length from the base of the cup to the tip of the petals.

The overall color is near Scarlet Red (HCC, page 19, shades 19/1–2) with Porcelain Rose (HCC, page 147, shades 20–20/1) at the center of the flower.

The petals average 30 to 35 in number plus several petaloidal stamens at the center of the flower, inserted regularly in the cup. In shape, the external petals have a rounded limbus with lateral edges slightly convergent in a robust base which is differentiated. The outer edge is smootn, slightly undulant and moderately rolled outwardly, forming one of several obtuse points at the juncture of the rolls. The central petals have dimensions slightly smaller than the guard petals and are concave at the center and slightly rolled at the outer edges, sometimes slightly creased. The base is arge, differentiated, and robust. The average dimensions of the guard petals are 55 to 65 mm. long and 60 to 70 mm. wide. The interior petals are 40 to 45 mm. in length and 50 to 60 mm. wide.

The color of the petals is, on the upper face, nearly Scarlet (HCC, page 19, shades 19–19/1–2–3) with shades of Porcelain Rose (HCC, page 147, shade 20) tinged with white toward the base. In the interior of the petals will often be noted a shade of Vermilion (HCC, page 18, shades 18/1–2). On the under face, the color of the petals is nearly Delft Rose (HCC, page 108, shades 020–020/1–2–3) sometimes with shades of Cherry Red (HCC, page 157, shade 722/2–3) in the outer petals. The base of the petals is nearly Aureoline Yellow (HCC, page 3, shades 3/1–2) tinged with white toward the border.

The surface of the petals is, on the upper face, velvety with reticulated radial veins slightly raised at the edge. The under face is satiny with veins slightly ridged at the edge.

*Reproductive Organs*—Stamens: Very numerous averaging 170 to 190, around the cup. The threads are thin, erect, slightly curved toward the center of the flower, and of a variable length from 5 to 15 mm. The anthers are of average dimensions, bisymmetrical, and terminated in threads. The styles are moderately numerous, at the center of the cup, surrounded by a bushy silky white down at their base. The styles range in length to 20 mm. and are very thin, twisted, gathered at the base, free standing, yellowish white and glandulous, averaging 110 to 120 in number.

The stigmata are fountain-shaped, terminated on the styles, and yellowish. The ovaries are raised, partly out of the cup.

*Odor*—Moderately strong, with midly fruity overtones.
*Resistance of Flowers to Climate*—Moderate
*Resistance of Flowers to Shipment*—Good.
*Durability of Cut Flowers*—Very good.
*Resistance of the Plant to Cryptogamic Diseases*—Good.
*Ease of Culture*—Very good.
*Compatibility with Ordinary Grafting Stock*—Very good.

Having described my invention, I claim:

1. The new and distinct variety of rose plant as described and illustrated.

No references cited.

ROBERT E. BAGWILL, Primary Examiner